US008323664B2

(12) United States Patent
Mitchell et al.

(10) Patent No.: US 8,323,664 B2
(45) Date of Patent: Dec. 4, 2012

(54) LIVE VACCINE STRAINS OF *FRANCISELLA*

(75) Inventors: Stephen Lloyd Mitchell, Salisbury (GB); Petra Claire Farquhar Oyston, Salisbury (GB); Richard William Titball, Salisbury (GB)

(73) Assignee: The Secretary of State for Defence (GB)

( * ) Notice: Subject to any disclaimer, the term of this patent is extended or adjusted under 35 U.S.C. 154(b) by 652 days.

(21) Appl. No.: 12/374,888

(22) PCT Filed: Jul. 25, 2007

(86) PCT No.: PCT/GB2007/002837
§ 371 (c)(1),
(2), (4) Date: Mar. 5, 2009

(87) PCT Pub. No.: WO2008/012538
PCT Pub. Date: Jan. 31, 2008

(65) Prior Publication Data
US 2010/0021501 A1    Jan. 28, 2010

Related U.S. Application Data (60) Provisional application No. 60/843,155, filed on Sep. 8, 2006.

(30) Foreign Application Priority Data

Jul. 25, 2006    (GB) ................... 0614743.3

(51) Int. Cl.
*A61K 39/02* (2006.01)
*C12N 1/20* (2006.01)
*C07H 21/04* (2006.01)

(52) U.S. Cl. .................. 424/234.1; 435/252.1; 536/23.1
(58) Field of Classification Search .................. None
See application file for complete search history.

(56) References Cited

U.S. PATENT DOCUMENTS

| 3,148,120 | A | 9/1964 | Otto |
| 4,235,871 | A | 11/1980 | Papahadjopoulos et al. |
| 4,235,877 | A | 11/1980 | Fullerton |
| 4,501,728 | A | 2/1985 | Geho et al. |
| 4,837,028 | A | 6/1989 | Allen |
| 4,912,094 | A | 3/1990 | Myers et al. |
| 5,019,369 | A | 5/1991 | Presant et al. |
| 5,066,596 | A | 11/1991 | Manning et al. |
| 5,187,074 | A | 2/1993 | Treiber et al. |
| 5,192,668 | A | 3/1993 | Treiber et al. |
| 5,278,302 | A | 1/1994 | Caruthers et al. |
| 5,308,854 | A | 5/1994 | Hoffman, Jr. et al. |
| 5,413,999 | A | 5/1995 | Vacca et al. |
| 5,476,874 | A | 12/1995 | Hungate et al. |
| 5,502,060 | A | 3/1996 | Thompson et al. |
| 5,578,597 | A | 11/1996 | Spector et al. |
| 5,663,169 | A | 9/1997 | Young et al. |
| 5,666,153 | A | 9/1997 | Copeland |
| 5,703,055 | A | 12/1997 | Felgner et al. |
| 5,846,978 | A | 12/1998 | Coburn et al. |
| 5,951,987 | A | 9/1999 | Cherwonogrodzky et al. |
| 6,261,568 | B1 | 7/2001 | Gicquel et al. |
| 6,268,171 | B1 | 7/2001 | Meyer et al. |
| 6,303,347 | B1 | 10/2001 | Johnson et al. |
| 6,350,454 | B1 | 2/2002 | Thune |
| 6,406,705 | B1 | 6/2002 | Davis et al. |
| 6,444,210 | B1 | 9/2002 | Kournikakis et al. |
| 6,444,445 | B2 | 9/2002 | Nikolich et al. |
| 6,444,804 | B1 | 9/2002 | Lam et al. |
| 6,544,518 | B1 | 4/2003 | Gerard et al. |
| 6,552,006 | B2 | 4/2003 | Raz et al. |
| 6,558,670 | B1 | 5/2003 | Friede et al. |
| 6,764,840 | B2 | 7/2004 | Johnson et al. |
| 7,399,756 | B2 | 7/2008 | Jomaa et al. |
| 7,588,744 | B1 | 9/2009 | Sylvester |
| 7,592,326 | B2 | 9/2009 | Karaolis |
| 8,198,430 | B2 | 6/2012 | Prior et al. |
| 2001/0024653 | A1 | 9/2001 | Gicquel et al. |
| 2003/0022226 | A1 | 1/2003 | Hooper et al. |
| 2004/0087555 | A1 | 5/2004 | Belmant et al. |
| 2006/0280759 | A1 | 12/2006 | Titball et al. |
| 2007/0066801 | A1 | 3/2007 | Engler et al. |
| 2007/0128225 | A1 | 6/2007 | Prior et al. |
| 2007/0218086 | A1 | 9/2007 | Tiollier |

(Continued)

FOREIGN PATENT DOCUMENTS
EP    0250614    1/1988

(Continued)

OTHER PUBLICATIONS

Pammit et al Infect. Immun. Apr. 2006 vol. 74 No. 4 2063-2071.*
Agarwal et al., Antisense therapeutics: is it as simple as complementary base recognition? Molecular Med, Today, 6:72-81, 2000. Abstract Only.
Agarwal et al., Medicinal chemistry and therapeutic potential of CpG DNA, Trends in Mol. Med., 8:114-121, 2002. Abstract Only.
Ascher et al., Modulation of Delayed-Type Hypersensitivity and Cellular Immunity to Microbial Vaccines; Effects of Cyclophosphamide on The Immune Response to Tularemia Vaccine, Infection and Immunity, 18(2): 318-323.
Broekhuijsen, et al., Genome-Wide DNA Microarray Analysis of *Francisella tularensis* Strains Demonstrates Extensive Genetic Conservation within the Species but Identifies Regions That Are Unique to the Highly Virulent *F. tularensis* subsp. *tularensis*, Journal of Clinical Microbiology, 41(7):2924-2931 (2003).
Buchele et al., Studies on pathogenesis and immunity in tularemia II. Immune response of the white rat to Bacterium tularense, Journal of Immunology, 63(2): 135-145 (1949).

(Continued)

Primary Examiner — Padma Baskar
(74) Attorney, Agent, or Firm — Kilpatrick Townsend & Stockton LLP (57) ABSTRACT

A strain of *Francisella* species wherein a gene which encodes for part of the glutamate metabolic pathway has been inactivated, and which is able to produce a protective immune response in an animal, for use as live prophylactic or therapeutic vaccine against infection by said *Francisella* species. Particularly effective strains include those where the capB gene is deleted. Other embodiments of the invention describe strains which comprise a further genetic mutation wherein a gene which encodes for another component of the cell is also inactivated. Pharmaceutical compositions comprising said strains, together with methods which utilize such strains are also described and claimed.

8 Claims, 8 Drawing Sheets

U.S. PATENT DOCUMENTS

| | | | |
|---|---|---|---|
| 2007/0264233 | A1 | 11/2007 | Michell et al. |
| 2007/0292386 | A9 | 12/2007 | Campbell et al. |
| 2008/0207568 | A1 | 8/2008 | Belmant |
| 2009/0087456 | A1 | 4/2009 | Eyles et al. |
| 2009/0196887 | A1 | 8/2009 | Morita et al. |
| 2010/0047283 | A1 | 2/2010 | Michell et al. |
| 2010/0080828 | A1 | 4/2010 | Prior |
| 2010/0119524 | A1 | 5/2010 | Ulaeto et al. |
| 2010/0204184 | A1 | 8/2010 | Montero et al. |
| 2012/0107360 | A1 | 5/2012 | Le Butt et al. |

FOREIGN PATENT DOCUMENTS

| | | |
|---|---|---|
| EP | 0362278 | 4/1990 |
| EP | 0109942 | 3/1991 |
| EP | 468520 | 1/1992 |
| EP | 671948 | 8/1997 |
| EP | 689454 | 9/1997 |
| EP | 2123285 | 11/2009 |
| GB | 2220211 | 1/1990 |
| GB | 2321103 | 7/1998 |
| GB | 2321103 A | 7/1998 |
| GB | 212666.2 | 7/2002 |
| GB | 0511722.1 | 6/2005 |
| GB | 0625587.1 | 12/2007 |
| GB | 2445028 A | 6/2008 |
| GB | 0906234.0 | 4/2009 |
| GB | 2469565 | 10/2010 |
| RU | 2240822 C2 | 4/2004 |
| WO | WO-88/08430 | 11/1988 |
| WO | 8809797 | 12/1988 |
| WO | 9111172 | 9/1991 |
| WO | WO-92/13871 | 1/1992 |
| WO | WO-93/11791 | 6/1993 |
| WO | 9402518 | 2/1994 |
| WO | 9421292 | 9/1994 |
| WO | 9514026 | 5/1995 |
| WO | 9517210 | 5/1995 |
| WO | 9526204 | 10/1995 |
| WO | 9633739 | 10/1996 |
| WO | WO-97/41234 | 11/1997 |
| WO | 9815287 | 4/1998 |
| WO | 9850399 | 11/1998 |
| WO | 9855148 | 12/1998 |
| WO | 9856414 | 12/1998 |
| WO | 9964301 | 12/1999 |
| WO | 000462 | 1/2000 |
| WO | WO0126683 A2 | 4/2001 |
| WO | 0146127 | 6/2001 |
| WO | WO0158485 | 8/2001 |
| WO | WO0218600 | 3/2002 |
| WO | WO-02/060935 | 8/2002 |
| WO | WO03068151 | 8/2003 |
| WO | WO-03/102191 | 12/2003 |
| WO | WO2004004654 A1 | 1/2004 |
| WO | WO2004084935 | 10/2004 |
| WO | WO2004098491 | 11/2004 |
| WO | WO2005013918 | 2/2005 |
| WO | WO-2005/021708 | 3/2005 |
| WO | WO-2005/054258 | 6/2005 |
| WO | WO-2005/063802 | 7/2005 |
| WO | WO-2006/067635 | 6/2006 |
| WO | WO-2006/103568 | 10/2006 |
| WO | WO2006111019 | 10/2006 |
| WO | WO2006131752 | 12/2006 |
| WO | WO2007028985 A2 | 3/2007 |
| WO | WO2007034166 | 3/2007 |
| WO | 200797789 | 8/2007 |
| WO | WO-2007/097789 | 8/2007 |
| WO | WO2008012538 | 1/2008 |
| WO | WO2008075075 | 6/2008 |
| WO | WO-2010/086617 | 8/2010 |
| WO | WO-2010/119245 | 10/2010 |

OTHER PUBLICATIONS

Burke, Immunization Against Tularemia Analysis of the Effectiveness of Live *Francisella tularensis* Vaccine in Prevention of Laboratory Acquired Tularemia, Journal of Infectious Diseases, 135(1): 55-60 (1977).

Candela, et al., Poly-gamma-glutamate in bacteria, Molecular Microbiology, 60(5):1091-1098 (2006).

Chen et al., Tularemia in BALB/c and and C57BL/6 mice vaccinated with *Francisella tularensis* LVS and challenged intradermally, or by aerosol with virulent isolates of the pathogen; protection varies depending on pathogen virulence, route of exposure, and host genetic background. Vaccine, 21:3690-3700, 2003.

Conlan, Vaccines against *Francisella tularensis*—past, present and future, Expert Rev. Vaccines, 3(3):307-314 (2004).

Drabick et al., Analysis of Active Live Immunization Versus Passive Humoral Immunotherapy Against Attenuated and Virule Strains of *Francisella tularensis*, Vaccine Research, 6(2): 67-74 (1997).

Dunstan, et al., Comparison of the Abilities of Different Attenuated *Salmonella typhimurium* Strains to Elicit Humoral Immune Responses against a Heterologous Antigen, Infection and Immunity, 66(2): 732-740 (1998).

Eigelsbach, et al., Prophylactic effectiveness of live and killed tularemia vaccines, I. production of vaccine and evaluation in the white mouse and guinea pig, Journal of Immunology, 87:415-425 (1961).

Ellis, et al., Tularemia, Clinical Microbiology Reviews, 15(4):631-646 (2002).

Eyles et al., Protection afforded against aerosol challenge by systemic immunisation with inactivated *Francisella tularensis* live vaccine strain (LVS), Microbial Pathogenesis 44:164-168, 2008.

Golovliov, et al., Adjuvanticity of ISCOMs incorporating a T cell-reactive lipoprotein of the facultative intracelluar pathogen *Francisella tularensis*, Vaccine, 13(3):261-267, Butterworth Heinemann (1995).

Golovliov, et al., A method for allelic replacement in *Francisella tularensis*, FEMS Microbiology Letters, 222:273-280 (2003).

Gray, et al., The identification of five genetic loci of *Francisella novicida* associated with intracellular growth, FEMS Microbiology Letters, 215:53-56 (2002).

Green, et al., Efficacy of the live attenuated *Francisella tularensis* vaccine (LVS) in a murine model of disease, Vaccine, 23:2680-2686 (2005).

Hartmann et al., Delineation of a CpG Phosphorothioate Oligodeoxynucleotide for Activating Primate Immune Responses in Vitro and in Vivo, Immunology, 164:1617-1624, 2000.

Hooper et al., DNA vaccination with Vaccinia Virus L1R and A33R Genes Protects Mice against a Lethal Poxvirus Challenge, Virology, 266:329-339 (2000).

Isherwood et al., Vaccination strategies for *Francisella tularensis*, Advanced Drug Delivery Reviews, Amsterdam, NL, 57(9):1403-1414 (2005).

Karlsson, et al., Sequencing of the *Francisella tularensis* Strain Schu 4 Genome Reveals the Shikimate and Purine Metabolic Pathways, Targets for the Construction of a Rationally Attenuated Auxotrophic Vaccine, Microbial & Comparative Genomics, 5(1):25-39 (2000).

Koskela et al., Cell-mediated immunity against *Francisella tularensis* after natural infection, Scandinavian Journal of Infectious Diseases, 12(4):281-287 (1980).

Krieg, The CpG motif: implications for clinical immunology, BioDrugs, 10(5):341-346, 1998. Abstract Only.

Larsson, et al., The complete genome sequence of *Francisella tularensis*, the causative agent of tularemia, Nature Genetics, 37(2):153-159 (2005).

Lavine et al., Immunization with heat-killed *Francisella tularensis* LVS elicits protective antibody-mediated immunity, Eur. J. Immunol., 37:3007-3020, 2007.

Law et al., Antibody Neutralization of the Extracellular Enveloped Form of Vaccinia Virus, Virology, 280, 132-142 (2001).

Lipman, et al., Rapid and Sensitive Protein Similarity Searches, Science, 227:1435-1441 (1985).

Mann et al., Rationally designed tularemia vaccines, Expert Rev Vaccines, 8(7):877-885, Jul. 2009.

McLendon, et al., *Francisella tularensis*: Taxonomy, Genetics, and Immunopathogenesis of a Potential Agent of Biowarfare, Annual Rev. Microbiol., 60:167-185 (2006).

Michell et al., Unpublished U.S. Appl. No. 10/550,773, filed Jul. 20, 2006.

Michell, et al., A capB mutant of *Francisella tularensis* subspecies tularenisis is attenuated in a mouse model of infection (Abstract MI 05) SGM Keele Meeting; XP002468651 (Sep. 12, 2005), Retrieved from the Internet URL:http://www.sgm.ac.uk/meetings/pdfabstracts/keele2005abs.pdf (2008).

O'Hagan, Recent developments in vaccine delivery systems, Current Drug Targets, Infectious Disorders, Bentham Science Publishers, Hilversum, NL, 1(3):273-286 (2001).

Overholt et al., An analysis of forty-two cases of laboratory-acquired tularemia. Treatment with broad spectrum antibiotics, The American Journal of Medicine, 30:785-806 (1961).

Oyston et al., Tularemia vaccine: past, present and future. Antonie van Leeuwenhoek, 87:277-281 (2005).

Pechous, et al., A *Francisella tularensis* Schu S4 Purine Auxotroph is Highly Attenuated in Mice but Offers Limited Protection Against Homologous Intranasal Challenge, PLoS One, 3(6): 1-10, 2008.

Pechous, et al, Construction and Characterization of an Attenuated Purine Auxotroph in a *Francisella tularensis* Live Vaccine Strain, Infection and Immunity, 74(8): 4452-4461, 2006.

Petrovsky et al., New-Age Vaccine Adjuvants: Friend or Foe?, BioPharm International.com, Aug. 2, 2007, 12 pgs.

Petrovsky, Freeing vaccine adjuvants from dangerous immunological dogma, Expert Rev. Vaccines 7(1), 7-10, 2008.

Quarry et al., A *Francisella tularensis* subspecies novicida purF mutant, but not a purA mutant, induces protective immunity to tularemia in mice. Vaccine, 25:2011-2018, 2007.

Robertson, et al., Detection of the Osmoregulator Betaine in Methanogens, Applied and Environmental Microbiology, 56:1504-1508 (1990).

Robertson, et al., β-Aminoglutaric acid is a major soluble component of *Methanococcus thermolithotrophicus*, Biochimica et Biophysica Acta, 992:320-326 (1989).

Rohmer, et al., Potential Source of *Francisella tularensis* Live Vaccine Strain Attenuation Determined by Genome Comparison, Infection and Immunity, 74(12):6895-6906, Dec. 2006.

Sandstrom, The Tularaemia Vaccine, J. Chem. Tech. Biotechnol., 59:315-320 (1994).

Sandstrom, et al., A Capsule-Deficient Mutant of *Francisella tularensis* LVS Exhibits Enhanced Sensitivity to Killing by Serum but Diminished Sensitivity to Killing by Polymorphonuclear Leukocytes, Infection and Immunity, 56(5):1194-1202 (1988).

Shen, et al., Mice sublethally infected with *Francisella novicida* U112 develop only marginal protective immunity against systemic or aerosol challenge with virulent type A or B strains of *F. tularensis*, Microbial Pathogenesis, 37:107-110 (2004).

Sorokin, et al., *Francisella tulaensis* resistance to bactericidal action of normal human serum, FEMS Immunology and Medical Microbiology, 13:249-252 (1996).

Svensson, et al., Evolution of Subspecies of *Francisella tularensis*, Journal of Bacteriology, 187(11):3903-3908 (2005).

Tarnvik et al., Stimulation of Human Lymphocytes by a Vaccine Strain of *Francisella tularensis*, Infection and Immunity, 12(5):951-957 (1975).

Tarnvik et al., Stimulation of Subpopulations of Human Lymphocytes by a Vaccine Strain of *Francisella tularensis*, Infection and Immunity, 20(3):698-704 (1978).

Tarnvik et al., Nature of Protective Immunity to *Francisella tularensis*, Review of Infectious Diseases, 11(3):440-451 (1989).

Tarnvik, et al., Orchestration of the protective immune response to intracellular bacteria: *Francisella tularensis* as a model organism, FEMS Immunology and Medical Microbiology, 13(3):221-225 (1996).

Tempel, et al., Attenuated *Francisella novicida* Transposon Mutants Protect Mice against Wild-Type Challenge, Infection and Immunity, 74(9):5095-5105, 2006.

Titball, et al., Will the enigma of *Francisella tularensis* virulence soon be resolved? TRENDS in Microbiology, 11 (3): 118-123 (2003).

Twine, et al., A Mutant of *Francisella tularensis* Strain SCHU S4 Lacking the Ability to Express a 58-Kilodalton Protein Is Attenuated for Virulence and Is an Effective Live Vaccine, Infection and Immunity, 73(12):8345-8352(2005).

Weiner, The immunobiology and clinical potential of immunostimulatory CpG oligodeoxynucleotides, Journal of Leukocyte Biology, 68:455-463, 2000.

Yamamoto et al., Ability of oligonucleotides with certain palindromes to induce interferon production and augment natural killer cell activity is associated with their base length, Antisense Research and Development, 4:119-122, 1994. Abstract Only.

Zhao et al., Effect of different chemically modified oligodeoxynucleotides on immune stimulation, Biochemical Pharmacology, 51:173-182, 1996. Abstract Only.

Database KEGG [Online] Feb. 19, 2007, 'Glutamate metabolism—*Francisella tularensis* subsp. *tularensis* SCHU S4,' XP002468730, Retrieved from HTTP://WWW.GENOME.JP/KEGG/PATHWAY/FTU/FTU00251.HTML.

"*Francisella tularensis*", Poster presented at ASM Meeting, Baltimore, MD Mar. 20-23, 2005, 11 pgs.

Genbank Accession No. AASP01000000.1, *Francisella tularensis* subsp. holarctica FSC200, whole genome shotgun sequence.

International Search Report dated Nov. 3, 2003 in International Application No. PCT/GB03/02338.

Alkhuder, et al., "Glutathione Provides a Source of Cysteine Essential for Intracellular Multiplication of *Francisella tularensis*", PLoS Pathogens 2009, 5:1-11.

Altschul, et al., "Basic Local Alignment Search Tool", Journal of Molecular Biology 1990, 215:403-410.

Altschul, et al., "Gapped BLAST and PSI-BLAST: a new generation of protein database search programs", Nucleic Acids Research 1997, 25(17):3389-3402.

Atkins, et al., "Cauterization of an acapsular mutant of Burkholderia pseudomallei identified by signature tagged mutagenesis", Journal of Medical Microbiol. 2002, 51(7):539-547.

Barker, et al., "Basis for the Failure of *Francisella tularensis* Lipopolysaccharide to prime human Polymorphonuclear leukocyte", Infection and Immunity 2006, 74(6), 3277-3284.

BéLanger, et al., "Functional analysis of genes responsible for the synthesis of the B-band O-antigen of *Pseudomonas aeruginosa* serotype 06 lipopolysaccharide", Microbiology 1999, 145:3505-3521.

Bosio, et al., "Active suppression of the pulmonary immune response by *Francisella tularensis* Schu4", Journal of Immunology 2007, 178:4538-4547.

Bowie, et al., "Deciphering the Message in Protein Sequences: Tolerance to Amino Acid Substitutions", Science 1990, 247:1306-1310.

Burrows, et al., "Molecular characterization of the *Pseudomonas aeruginosa* serotype O5 (PAO1) B-band lipopolysaccharide gene cluster", Molecular Microbiology 1996, 22:481-495.

Carlsson, et al., "Enzyme-Linked Immunosorbent Assay for Immunological Diagnosis of Human Tularemia", Eur. J. Brioche. 2002, 269:6112-6118 pgs.

Casetti, et al., "Drug-Induced Expansion and Differentiation of Vy9Vo2 T Cells in Vivo: The role of exogenous IL-2", Journal of Immunology 2005, 1593-1599.

Chamberlain, "Evaluation of Live Tularemia Vaccine Prepared in a Chemically Defined Medium", Applied Microbiology 1965, 13(2):232-235.

Champion, et al., "Comparative genomic characterisation of *Francisella tularensis* strains", PLoS Pathogens 2009, 5:e1000459.

Chart, "Lipopolysaccharide : Isolation and Characterization", In: Raton B, Arbor A (eds.) Methods in Practical Laboratory Bacteriology, CRC Press, London, Tokyo 1994, 11-20.

Clemens, et al., "Virulent and Avirulent Strains of *Francisella tularensis* Prevent Acidifcation and Maturation of Their Phagosomes and Escape Into the Cytoplasm in Human Macrophages", Infection and Immunity 2004, 72(6):3204-3217.

Conlan, et al., "Different host defences are required to protect mice from primary systemic vs pulmonary infection with the facultative intracellular bacterial pathogen, *Francisella tularensis* LVS", Microb. Pathog. 2002, 32:127-134.

Cowley, et al., "Isolation and characterization of *Francisella novicida* mutants defective in lipopolysaccharide biosynthesis", FEMS Microbiol Lett. 2000, 182:63-67.

Davis, et al., "Pathology of Experimental Pneumonic Plague Produced by Fraction-1 Positive and Fraction-1 Negative *Yersinia pestis* in African Green Monkeys (*Cercopithecus aethiops*)", Arch. Pathol. Lab. Med 1996, 120(2):156-163.

Deng, et al., "Identification of Francisella tularensis genes affected by iron limitation" Infect. Immun., 2006, 74:4224-4236.

Drabick, et al., "Passive Protection of Mice against Lethal *Francisella tularensis* (Live Tularemia Vaccine Strain) Infection by the sera of human recipients of the Live Tularemia Vaccine", The American Journal of the Medical Sciences 1994, 308:83-87.

Dreisbach, et al., "Purified Lipopolysaccharide from *Francisella tularensis* Live Vaccine Strain (LVS) Induces Protective Immunity against LVS Infection That Requires B Cells and Gamma Interferon", Infection and Immunity 2000, 68:1988-1996.

Eigelsbach, et al., "Murine Model for Study of Cell-Mediated Immunity: Protection Against Death from Fully Virulent *Francisella tularensis* Infection", Infection & Immunity 1975, 12(5): 999-1005.

EMBL-Bank Sequence Database, Accession No. AF140738, Jan. 19, 2000.

Florence, et al., "Formulation in vol. 5 of Comprehensive Medicinal Chemistry, Corwin Hansch; Chairman of Editorial Board", Pergamon Press 1990, 567-591.

Forest, et al., "Type IV pili structure, assembly and immunodominance: applications to vaccine design", Vaccines 1997, 97:167-173.

Forslund, et al., "Direct repeat-mediated deletion of a type IV pilin gene results in major virulence attenuation of *Francisella tularensis*", Molecular Microbiology 2006, 59(6):1818-1830.

Forslund, et al., "Type IV Pili is Required for Virulence of *Francisella tularensis*", Abstract, American Society of Microbiology Biodefense Research meeting, Mar. 20-23, 2005.

Fulop, et al., "Production and Characterization of Monoclonal Antibodies Directed against the Lipopolysaccharide of *Francisella tularensis*", Journal of Clinical Microbiology 1991, 29:1407-1412.

Fulop, et al., "Role of antibody to lipopolysaccharide in protection against low- and high virulence", Vaccine 2001, 19:4465-4472.

Fulop, et al., "Role of lipopolysaccharide and a major outer membrane protein from *Francisella tularensis* in the induction of immunity against tularaemia", Vaccine 1995, 13(13):1220-1225.

Fulop, et al., "Role of two outer membrane antigens in the induction of protective immunity against *Francisella tularensis* strains of different virulence", FEMS Immunology and Medical Microbiology 1996, 13:245-247.

Gil, et al., "Presence of Pili on the Surface of *Francisella tularensis*", Infection and Immunity 2004, 3042-3047.

Gossman, et al., "Quantitative Structure-Activity Relations of yo T Cell Activation by Phosphoantigens", Journal of Med. Chem. 2002, 45:4868-4874.

Greenspan, et al., "Defining Epitopes: Its not as easy as it seems", Nature Biotechnology 1999, 7:936-937.

Groisman, "How bacteria resist killing by host-defense peptides", Trends Microbiol 1994, 2:444-449.

Hahn, et al., "The type-4 pilus is the major virulence-associated adhesin of *Pseudomonas aeruginosa*—a review", Gene 1997, 99-108.

Hatch, et al., "Immunogenic Substances in culture filtrates and lysates of *Pasteurella tularensis*", Journal of Bacteriology Sep. 1964, vol. 88(3), 566-573.

Hertle, et al., "Dual-function vaccine for *Pseudomonas aeruginosa*: characterization of a chimeric exotoxin A-pilin protein", Infection and Immunity 2001, 69(11):6962-6969.

Hollis, et al., "*Francisella philomiragia* comb. Nov. (Formerly *Yersinia philomiragia*) and *Francisella tularensis* Biogroup Novicida(Formerly *Francisella novicida*) Associated with Human Disease", Journal of Clinical Microbiology 1989, 27(7):1601-1608.

Hubalek, et al., "Comparative proteome analysis of cellular proteins extracted from highly virulent *Francisella tularensis* ssp. *tularensis* and less virulent *F. tularensis* ssp. *holarctica* and *F. tularensis* ssp. *mediaasiatica*", Proteomics 2004, 4:3048-3060.

Johnson, et al., "Routes of Administration and Dosage Regimes", Comprehensive Medicinal Chemistry 1990, 5:593-613.

Kadzhaev, et al., "Identification of genes contributing to the virulence of *Francisella tularensis* SCHU S4 in a Mouse Intradermal Infection Model", PLoS One 2009, 4.

Kawula, et al., "Use of Transposon-Transposase Complexes to Create Stable Insertion Mutant Strains of *Francisella tularensis* LVS", Applied and Environmental Microbiology 2004, 70:6901-6904.

Kenne, et al., "Bacterial Polysaccharides, The Polysaccharides", Molecular Biology 1983, vol. 2, pp. 287-362.

Khlebnikov, et al., "Outer Membrane of a lipopolysaccharide-protein complex (LPS-17 KdA Protein) as chemical *tularemia* vaccines", FEMS Immunology and Medical Microbiology 1996, 13:227-33.

Kieffer, et al., "*Francisella novicida* LPS has greater immunobiological activity in mice than *F. tularensis* LPS, and contributes to *F. novicida* murine pathogenesis", Microbes and Infection 2003, 5:397-403.

Kiss, et al., "Characterization of fig operon mutants of *Francisella novicida* U112", FEMS Micriobiol. Letters 2008, 270-277.

Knirel, et al., "Somatic antigens of *Pseudomonas aeruginosa*", Eur. J. Brioche. 1985, 150:541-550.

Kuolee, et al., "Vaccines and therapeutic agents for tularemia", Informa Healthcare 2007, 267-275.

Kus, et al., "Significant differences in type IV pilin allele distribution among *Pseudomonas aeruginosa* isolates from cystic fibrosis (CF) versus non-CF patients", Microbiology 2004, 150:1315-1326.

Laemmli, "Cleavage of structural Proteins during the Assembly of the Head of Bacteriophage T4", Nature 1970, 227, pp. 680-685.

Lai, et al., "Expression of IgIC is necessary for intracellular growth and induction of apoptosis in murine macrophages by *Francisella tularensis*", Microbial Pathogenesis 2004, 37:225-230.

Larsson, et al., "Molecular evolutionary consequences of niche restriction in *Francisella tularensis*", PLoS Pathogens 2009, 5:e1000472.

Lascola, et al., "Rapid comparative genomic analysis for clinical microbiology", Genome Res 2008, 18:742-750.

Lauriano, et al., "MgIA regulates transcription of virulence factors necessary for *Francisella tularensis* intraamoebae and intramacrophage survival", Proc. Natl. Acad. Sci. USA 2004, 101:4246-4249.

Mack, et al., "A new cell Assay to Determine the Virulence of *Francisella tularensis*", Letters in Applied Microbiology 1994, 19:158-160.

Maier, et al., "In Vivo Himarl1-Based Transposon Mutagenesis of *Francisella tularensis*", Applied Environmental Microbiology 2006, 72(3):1878-1885.

McMurry, et al., "Diversity of *Francisella tularensis* Schu4 antigens recognized by T lymphocytes after natural infections in humans: identification of candidate epitopes for inclusion in a rationally designed tularemia vaccine", Vaccine 2007, 25(16):3179-91.

Mitchell, et al., "Development of real-time PCR assays for the specific detection of *Francisella tularensis* ssp. *tularensis, holarctica and mediaasiatica*", Molecular and Cellular Probes 2010, 24:72-76.

Nano, et al., "A *Francisella tularensis* Pathogenicity Island Required for Intramacrophage Growth", Journal of Bacteriology 2004, 186(19):6430-6436.

Narayanan, et al., "Immunotherapy of Tularemia: Characterisation of a monoclonal antibody reactive with *Francisella tularensis*", Journal of Leukocyte Biology 1993, 53:112-116.

Nielsen, et al., "Peptide nucleic acids (PNAs): Potential anti-sense and anti-gene agents", Anti-Cancer Drug Des. 1993, 8:53-63.

Nutter, et al., "Antigens of *Pasteurella tularensis*: Preparative Procedures", Applied Microbiology Jul. 1971, vol. 22(1), 44-48.

Olsufiev, et al., "Comparative study of strains of *B. tularense* in the old and New World and their Taxonomy", J. Hyg. Epidemiol. Microbiol. Immunol. 1959, 3:138-149.

Ormsbee, et al., "Studies on Bacterium Tularense Antigens, I. The Isolation, Purification and Biologic Activity of Antigen Preparations from Bacterium tularense", Journal of Immunology 1954, 74:351-358.

Ormsbee, et al., "Studies on Bacterium Tularense Antigens, II. Chemical and Physical Characteristics of Protective Antigen Preparations", Journal of Immunology 1954, 74:359-370.

Pavlov, et al., "Cryptic plasmid pFNL10 from *Francisella novicida*-like F6168: the base of plasmid vectors for *Francisella tularensis*", FEMS Immunol. Med. Microbiol. 1996, 13:253-256.

Petrosino, et al., "Chromosome rearrangement and diversification of *Francisella tularensis* revealed by the type B (OSU18) genome sequence", J. Bacteriol 2006, 188(19):6977-85.

Poquet, et al., "Expansion of Vγ9Vδ2 T Cells Is Triggered by *Francisella tularensis*-Derived Phosphoantigens in Tularemia but Not after Tularemia Vaccination", Infection and Immunity 1998, 2107-2114.

Prior, et al., "Preliminary analysis and annotation of the partial genome sequence of *Francisella tularensis* strain Schu 4", Journal of Applied Microbiology 2001, 91:614-620.

Qin, et al., "Identification of an essential *Francisella tularensis* subsp. tularensis Virulence Factor", Infection and Immunity 2009, 152-161.

Qin, et al., "Identification of transposon insertion mutants of *Francisella tularensis* strain Schu S4 deficient in intracellular replication in the hepatic cell line HepG2", BMC Microbiology 2006, 6:69.

Reed, et al., "A simple Method of Estimating Fifty Per Cent Endpoints", Am. J. Hygiene 1938, 27(3):493-497.

Richards, et al., "Identification of *Francisella* genes up-regulated in the macrophage", Poster at the International Conference on *tularemia* Nov. 2006.

Rohmer, et al., "Comparison of *Francisella tularensis* genomes reveals evolutionary events", Genome Biol. 2007, 8:R102.

Roper, et al., "Extracellular Vaccine Virus Envelope Glycoprotein Encoded by the A33R Gene", Journal of Virology 1996, 70(6):3753-3762.

Russell, et al., "The efficacy of ciprofloxacin and doxycycline against experimental tularemia", J. Antimicrob. Chemother. 1998, 41:461-5.

Salomonsson, et al., "A Role for a Type IV Pilus in Virulence of *Francisella tularensis*", Abstract, Society of General Microbiology, 155th Meeting, Sep. 6-9, 2004, Trinity College, Dublin, Ireland 2004.

Salomonsson, et al., "A Role for a Type IV Pilus in Virulence of *Francisella tularensis*", Abstract, American Society for Microbiology Meeting, Jun. 5-9, 2005 May 2005.

Samrakandi, et al., "Genome diversity among regional populations of *Francisella tularensis* subspecies", FEMS Microbiology Letters 2004, 237:9-17.

Sandstrom, et al., "Antigen from *Francisella tularensis*: Nonidentity Between Determinants Participating in Cell-Mediated and Humoral Reactions", Infect. Immun. 1984, 12(1):101-106.

Sanger, et al., "DNA sequencing with chain-terminating inhibitors", Proc. Natl. Acad. Sci. U.S.A. 1997, 74:5463-5467.

Sonnhammer, et al., "A hidden Markov model for predicting transmembrane helicesinprotein sequences", In: Glasgow S, Littlejohn T et al. (eds.) , 175-182.

Su, et al., "Genome-Wide Identification of *Francisella tularensis* Virulence Determinants", Infection and Immunity 2007, 3089-3101.

Sullivan, et al., "Characterization of the Siderophore of *Francisella tularensis* and Role of fslA in Siderophore production", Journal of Bacteriology 2006, 188:3785-3795.

Tonjum, et al., "The pilus colonization factor of pathogenic neisserial species: organelle biogenesis and structure/function relationships—a review", Gene 1997, 155-163.

Vinogradov, et al., "Structural Analysis of *Francisella tularensis* Lipopolysaccharide", Eur. J. Brioche. 2002, 269: 6112-6118.

Vogel, et al., "Acetylornithinaase of *Escherichia coli*: Partial Purification and some Properties", J. Biol. Chem. 1955, 218:97-106.

Waag, et al., "Cell-Mediated and humoral immune responses after vaccination of human volunteers with the live vaccine strain of *Francisella tularensis*", Clin. Diagn. Lab. Immunol 1995, 2:143-148.

Waag, et al., "Immunogenicity of a new lot of *Francisella tularensis* live vaccine strain in human volunteers", FEMS Immunol. Med. Microbiol. 1996, 13:205-209.

Waldo, et al., "Proteome Cataloging and relative quantification of *Francisella tularensis* strain Schu4 in 2D Page using preparative isoelectric focusing", Journal of Proteome Research , 6(9): 3484-3490.

Westphal, et al., "Bacterial Lipopolysaccharides", Methods in Carbohydrate Chemistry, Ed. Roy L. Whistler, Academic Press 1965, 5: 83-91.

Whitfield, et al., "Modulation of the surface architecture of gram-negative bacteria by the action of surface polymer:Lipid A-core ligands and by determinants of polymer chain length", Mol. Micro. 1997, 23(4):629-638.

Tularemia, located at http://www.nlm.nih.gov/medlineplus/ency/article/000856.htm, downloaded Jun. 28, 2011.

Search Report dated Aug. 3, 2011 in International Application No. PCT/GB2010/000743.

Search Report dated Aug. 7, 2009 in Application No. GB0906234.0.

Search Report dated Aug. 13, 2010 in Application No. GB1006165.3.

Ascher et al., Clin. Exp. Immunology, 1980, 41: pp. 225-226.

Atlas, "Handbook of Microbiological Media", Thayer-Martin Agar, Modified; erd Ed., CrC Press, FLA, 2004, 1365-1369.

Chain et al., "Complete genome sequence of *Francisella tularensis* LVS (Live Vaccine Strain)", NCBI Reference Sequence: NC_007880.1, 2012.

Dalsgaard, "Saponin Adjuvants", 1974, 243-254.

Golovliov et al., "Indentification of proteins of *Francisella tularensis* induced during growth in macrophages and cloning of the gene encoding a prominently induced 23-kilodalton protein", Infect. Immun. 65(6): 2183-2189, 1997.

Hartley et al., "Grey variants of the line vaccine strain of *Francisella tularensis* lack lipopolysaccharide O-antigen, show reduced ability to survive in macrophages and do not induce protective immunity in mice", Vaccine, 24:989-996, 2006.

Huseby et al., "Practical points regarding routine determination of γ-glutamyl transferase (γ-GT) in serum with a kinetic method at 37°C.,", Scandinavian Journal Clin. Lab. Invest., 34:357-363, 1974.

Johansson et al., "Worldwide Genetic Relationships among *Francisella tularensis* Isolates Determined by Multiple-Locus Variable-Number Tandem Repeat Analysis", Journal of Bacteriology, 186(17):5808-5818, 2004.

Kadzhaev et al., "Identification of Genes Contributing to the Virulence of *Francisella tularensis* Schu S4 in a Mouse Intradermal Infection Model", PLoS One, 2009, vol. 4, Issue 5, e5463; 1-11.

McCrumb et al., "Aerosol Infection of Man with *Pasteurella tularensis*", Bacteriol Rev., 25(3):262-7, 1961.

Salyers et al., "Vaccines and Other Approaches to Modulating the Immune Response", Bacterial Pathogenesis A Molecular Approach, 1994, 90.

Sambrook et al., "Molecular Cloning", Molecular Cloning: A laboratory Manual, 2001, 3rd ed., Spring Harbor laboratory New York, NY, 2001; v-xx.

Simon et al., "A broad host range mobilisation system for in vitro genetic engineering: transposon mutagenesis in Gram-negative bacteria", Biotechnology, 1:784-791, 1983.

Szoka , "Comparative Properties and Methods of Preparation of Lipid Vesicles (Liposomes)", Ann. Rev. Biophy. Bioeng., 9:467-508, 1980.

Tigertt , "Soviet viable Pasteurella tularensis vaccines", Bacteriol. Rev. 26:354-373, 1962.

\* cited by examiner

Figure 1

Genomic arrangement of capB locus in wildtype F. tularensis SchuS4

- SchuS4Δ*capB* 1.6x10⁶ cfu
- SchuS4Δ*capB* 1.6x10⁵ cfu
- SchuS4Δ*capB* 1.6x10⁴ cfu
- naïve controls All mice challenged with 70cfu SchuS4

LIVE VACCINE STRAINS OF *FRANCISELLA*

CROSS REFERENCE TO RELATED APPLICATIONS

This application is the U.S. national phase of International Application No. PCT/GB2007/002837 filed on Jul. 25, 2007 and published in English on Jan. 31, 2008 as International Publication No. WO 2008/012538 A2, which application claims priority to Great Britain Application No. 0614743.3 filed on Jul. 25, 2006 and U.S. Provisional Application Ser. No. 60/843,155 filed on Sep. 8, 2006, the entire contents of all of which are incorporated herein in their entireties by reference.

This invention relates to live strains of *Francisella* species, their use as prophylactic or therapeutic vaccines, to compositions comprising these strains, and their use in the prevention or treatment of bacterial infection.

*Francisella tularensis* is an extremely pathogenic Gram-negative bacterium and is the etiological agent of the zoonotic disease Tularemia. There are four recognised sub-species of *F. tularensis*, including subspecies *tularensis, holarctica*, and *novicida*, which exhibit a high degree of genetic conservation. The most virulent subspecies is *Francisella tularensis* subspecies *tularensis*, which has an infectious dose in humans of as little as 10 cells via the airbourne route.

At present there is no available vaccine against *F. tularensis* infection although it has been demonstrated previously that an undefined attenuated strain of *Francisella tularensis*, which has been designated *Francisella tularensis* live vaccine strain (LVS), is capable of providing protection against the most virulent subspecies, tularensis. However, the LVS vaccine is not registered and has only been used to vaccinate at-risk, individuals under special license. This license has now been withdrawn. The LVS strain is likely to remain unlicensed because the genetic changes that are responsible for the attenuating phenotype are not understood at the molecular level. Therefore, there exists a possibility that the vaccine strain could revert back to the fully virulent form. Further, it has been shown that whilst LVS provides effective protection in the mouse model of infection, protection is not complete. The protection afforded by LVS against an aerosol challenge of the most virulent tularensis subspecies is sub-optimal. Clearly, a vaccine which is genetically stable and which provides complete protection is highly desirable.

The fact that naturally occurring, attenuated strains of *F. tularensis* can induce protective immunity does suggest that an attenuated strain with properly defined genetic mutations in the organism's virulence factors is a feasible approach in vaccine development.

Unfortunately, however, relatively little is known about the virulence mechanisms of *F. tularensis* and, as such, virulence factors have proven to be very difficult to predict; the recent completion of the genome sequence of the virulent strain *F. tularensis* subspecies *tularensis* SchuS4 has so far failed to reveal the presence of classical virulence factors such as toxins or type-III secretion systems, which are predominant in so many other pathogenic bacteria.

Some efforts to identify new vaccine strains have focused on naturally occurring strains (other than LVS) or on spontaneously attenuated strains of *F. tularensis*, such as the FSC043 mutant of SchuS4 reported by Twine et al (*Infection and Immunity* Vol 73, 2005, pp 8345-8352). Examination of these attenuated mutants has confirmed that mutations can lead to attenuated strains which afford some level of protection against tularemia. However, the molecular basis of this attenuation and protection is unknown and, in any case, the protection afforded is not better than that provided by LVS. The problem remains, therefore to find defined mutations which give complete protection against the most virulent forms of *Francisella*.

A live vaccine strain of *Francisella* derived from the sub-species *novicida*, which contains a single genetic mutation, is described in co-pending International Application number PCT/GB2004/001264, the contents of which are hereby incorporated by reference. This application shows that a genetic lesion in the purine enzyme pathway provides attenuated strains which are also protective in the mouse model of infection. Whilst this clearly represents a significant advance in the development of a vaccine for tularemia, it is widely recognised that an additional genetic mutation would be required to enable such a strain to obtain licensed status. The problem remains, therefore, to determine further mutations which result in attenuated strains but which also provide complete protection against all strains of *Francisella tularensis*.

New live vaccines, containing well defined mutations and which are fully protective against tularemia are therefore required.

The applicants have found that by modifying strains of *Francisella* in a particular way, attenuated strains which are protective can be produced. These live strains can be used as the basis for new vaccines against tularemia.

The present invention therefore provides a strain of *Francisella* species wherein a gene which encodes for part of the glutamate metabolic pathway has been inactivated, and which is able to produce a protective immune response in an animal, for use as a live prophylactic or therapeutic vaccine against infection by said *Francisella* species.

As used herein, the term "metabolic pathway" means the sum total of the chemical processes occurring in a cell, in which the processes occur in steps, through which compounds are gradually built up or broken down. Each step of the metabolic pathway is catalysed by an enzyme, whose structure is encoded by a gene.

As used herein the term "glutamate metabolic pathway" means the chemical processes whereby glutamate is synthesised or broken down, including those steps wherein an enzyme catalyses the formation of glutamate or catalyses the use of glutamate to form another material.

Thus, genes that encode for part of the metabolic pathway in *Francisella* species include those genes which encode for the formation of glutamate and those which encode for enzymes which are utilised in the glutamate metabolic pathway. Inactivation of such a gene is likely to interrupt the normal metabolic pathway such that, for example, glutamate is not produced by the cell or that the amount of glutamate produced is significantly altered when compared with the virulent *Francisella* species, such as *Francisella tularensis* subspecies *tularensis* SchuS4, in which the same gene having been inactivated.

The presence, or absence, of glutamate (or aminoglutaric acid) may be readily determined using 13C, 15N or 1H Nuclear Magnetic Resonance Spectroscopy (NMR), as described by the papers by Robertson, D. E. et al (*Applied and Environmental Microbiology* 1990, vol. 56 pp 1504-1508 and *Biochimica et Biophysica Acta* 1989, vol. 992, pp 320-326) and the quantities of glutamate produced by strains of the present invention may be readily determined using techniques such as Liquid Chromatography-Mass Spectrometry (LC-MS), which are routine in the art.

As used herein "glutamate" refers to the amino acid glutamate or glutamic acid, which may exist in the form of β-glutamate (beta-glutamate) or γ-glutamate (gamma-glutamate).

The inventors have found that inactivating a gene which encodes for part of the glutamate metabolic pathway provides a strain which is both attenuated and protective against exposure to virulent *Francisella* species. Without wishing to be bound by theory, it is thought that part of the glutamate metabolic pathway may include, or have an effect on the formation of extracellular capsule. Thus, genes which encode for the synthesis of capsule, or which are analogous to these genes when compared with established capsule encoding genes from other organisms, may fall within the definition of genes that encode for part of the metabolic pathway, as described above.

As used herein, the term "capsule" means an extracellular component, commonly a layer, of polysaccharide and/or protein which protects a bacterial cell and which, in association with pathogenic bacteria, serves as a barrier against phagocytosis by the white blood cells of an animal host, in which the pathogenic bacteria are present.

As used herein, the term "capsule-encoding gene" means a gene which encodes for a protein, or other molecule, which is involved in the synthesis of the capsule component of a bacterial cell or a gene which is homologous to a gene which has been assigned as having some involvement in bacterial capsule biosynthesis, including involvement in the synthesis of capsule or any component thereof and involvement in the assembly and/or transport of said components to form a capsular structure.

As used herein, the terms "homologous" and "homology" means, at the protein level, the similarity of two amino acid sequences are such that the two sequences share greater than 30% identity. Identity in this instance can be judged for example using the BLAST program (vs. 2.2.12) found at http://www.ncbi.nim.nih.gov/BLAST/ or the algorithm of Lipman-Pearson with, for example, Ktuple:2, gap penalty:4, Gap Length Penalty:12, standard PAM scoring matrix or other suitable parameters as readily determined by a person skilled in the art (Lipman, D. J. and Pearson, W. R., Rapid and Sensitive Protein Similarity Searches, *Science*, 1985, vol. 227, 1435-1441).

Genes which encode for the glutamate metabolic pathway (including those which encode for a capsule component) of the *Francisella* bacterium may be determined by analysis of the relevant genome sequence and/or by comparison with other bacteria which have well-defined capsule encoding genes.

Gene inactivation can be carried out using any of the conventional methods known in the art. Typically, the strain is transformed with a vector which has the effect of down-regulating or otherwise inactivating the gene. This can be done by mutating control elements such as promoters and the like which control gene expression, by mutating the coding region of gene so that any product expressed is inactive, or by deleting the gene entirely. Alternatively, the gene can be inactivated at the RNA or protein level, by transforming the cell so that it expresses a sense or anti-sense construct which binds to DNA or RNA encoding the gene to prevent transcription thereof.

Preferably however, the gene is inactivated by complete or partial deletion mutation or by insertional mutation.

Specifically, the applicants have found that it is preferable to inactivate one or more of the genes which has been annotated in the *Francisella tularensis* genome as being a capsule-encoding gene, for example capB or capC (hereinafter "cap" genes). In particular the applicants have found that it is preferable to inactivate a cap gene in *Francisella* species such as *F. tularensis* subspecies *tularensis* or subspecies *holarctica*. In a preferred embodiment, the capB gene (FTT0805) and/or the capC gene (FTT0806) of *F. tularensis* subspecies *tularensis* is inactivated to provide one strain according to the present invention. In other embodiments, the corresponding genes of other *Francisella* species are deleted to provide other strains according to the preset invention. The corresponding cap genes from other *Francisella* species will usually have at least 80%, preferably at least 85% homology and more preferably at least 90% homology to, and similar function to, the cap genes of *F. tularensis* subspecies *tularensis*. In a more preferred embodiment, the capB gene (FTT0805) of *F. tularensis* subspecies *tularensis* strain SchuS4 is inactivated to provide a preferred strain.

In particular, the applicants have found that a strain of *Francisella tularensis* which has a cap gene inactivated is attenuated and is protective against challenge from virulent *Francisella* species. As illustrated hereinafter, a strain of *F. tularensis* subspecies *tularensis* which has an inactivated cap gene is protective in mice. In particular the applicants have shown that deletion of the capB gene from *F. tularensis* subspecies *tularensis* SchuS4 strain provides an attenuated strain which is protective against aerosol challenge with the virulent SchuS4 strain.

The strain of the invention suitably has a further defined mutation or lesion so as to reduce the risk of the bacterium reverting to a virulent form. In this case, the mutation is in a gene which is selected so that the strain is suitably attenuated, but can still retain the ability to stimulate a sufficient immune response to provide long term protection. Suitable additional mutations can be identified using conventional methods, and examination and analysis of the current live vaccine strain (LVS) or other attenuated strains may assist in the identification. Examples of these mutations include, but are not limited to, mutations to the FTT0918 and FTT0919 genes. Alternatively the further defined mutation may advantageously involve a gene which encodes for another component of the cell, which is not part of the glutamate metabolic pathway. Such further mutations include, but are not limited to, mutations which inactivate pilin genes, for example mutations to pilA and/or pilE and/or pilC genes or other mutations such as those described in co-pending British patent application number GB0511722.1 (the contents of which are hereby incorporated by reference), mutations which inactivate genes which encode enzymes in the purine pathway, for example mutations to purA and/or purF genes and other purine pathway genes such as those described in co-pending International Application number PCT/GB2004/001264 (the contents of which are hereby incorporated by reference).

Particular preferred examples of further defined mutations are inactivation of the purF and/or inactivation of the pilA gene and/or inactivation of the FTT0918 gene.

It will be understood by the skilled person that such further defined mutations can be achieved by using any conventional method as hereinbefore described but that in preferred embodiments of the inventions the gene which encodes for other components of the cell is inactivated by complete or partial deletion mutation or by insertional mutation.

Since the strains of the present invention have been found to be protective against infection by *Francisella* species in the mouse model of infection, the strains also provide useful vaccines against the diseases caused by *Francisella* infections and, in particular, tularemia. It is therefore preferred that the strains are formulated into pharmaceutical compositions, in which they are combined with a pharmaceutically acceptable carrier. Such pharmaceutical compositions form a second aspect of the invention.

Suitable carriers may be solid or liquid carriers as is understood in the art. They may suitably be formulated for administration to mucosal surfaces (for example for oral use, of for administration by inhalation or insufflation) or for parenteral administration.

In particular they are formulated as sterile aqueous or oily solutions for intravenous, subcutaneous, intramuscular or intramuscular dosing.

Alternatively they are formulated for administration to mucosal surfaces and in particular for intranasal application. Such formulations may include microencapsulation of the strain in the composition, or microencapsulation of the entire composition. Such microencapsulation techniques are commonly known in the art.

Compositions are suitably prepared in unit dosage forms, as conventional in the art. They are administered at dosages which are determined using clinical practice, and depend upon factors such as the nature of the patient, the severity of the condition, and the precise vaccine strain being employed. Typically dosage units will comprise $10^5$-$10^8$ cfu. Dosages may be boosted as appropriate or necessary.

Compositions may also contain further immunogenic reagents which are effective against *F. tularensis* infection or other diseases. They may further contain other agents such as adjuvants and the like, which enhance the host's immune response to the vaccine.

In a further aspect the present invention relates to the use of a strain of *Francisella* species wherein a gene which encodes for part of the glutamate metabolic pathway has been inactivated, and which is able to produce a protective immune response in an animal, in the preparation of a live prophylactic or therapeutic vaccine against infection by *Francisella* species. In particular, such strains find use in the preparation, or manufacture, of a vaccine for the treatment of Tulaaremia.

In yet a further aspect, the invention provides a method of preventing or treating infection caused by *Francisella* species, which method comprises administering to an animal, including a human being, an effective amount of a strain or of a pharmaceutical composition, each as hereinbefore described.

In particular, the method is useful in the treatment of infection caused by *Francisella tularensis* subspecies *tularensis*.

Novel strains which are suitable for vaccine use form a further aspect of the invention. In particular, the invention provides a strain of *Francisella* species wherein a gene which encodes for part of the glutamate metabolic pathway has been inactivated. In particular the strains which are suitable for use as vaccines are as hereinbefore described. In a preferred embodiment the inactivated gene is capB or capC. It is further preferred that the strain is a strain of *Francisella tularensis* subspecies *tularensis*, for example the SchuS4 strain.

The invention will now be particularly described by way of non-limiting Example, with reference to the accompanying diagrammatic drawings in which.

EXAMPLE 1

Construction of a Plasmid Containing a Mutated Allele of *F. tularensis* capB

The capB gene of *F. tularensis* subspecies *tularensis* strain SchuS4 encodes a protein of 405 amino acids (aa) that has 36% identity to the 397 aa CAPB protein from *Bacillus anthracis* strain 'Ames Ancestor'. Regions of DNA flanking the capB gene of *F. tularensis* were PCR amplified from *F. tularensis* subspecies tularensis strain SchuS4 using the primer pairs P1/P2 and P3/P4 as shown in Table 1. The chloramphenicol resistance cassette (Cam-r) was PCR amplified from the plasmid pKK202 with the primer pair CamF/CamR.

TABLE 1

Primers used for the construction of pSMP42 - Sequences in bold indicate the sequence complementary to Francisella DNA and the underlined sites in the 5' extensions are restriction sites.

| P1 | 5'-CTG<u>ACGCGT</u>-AGGCAGTGTGGTTATGGGTAG-3' |
|---|---|
| P2 | 5'-GAC<u>GGTAACC</u>-CAAATACGACGACAATTAAC-3' |
| P3 | 5'-CTG<u>GGTAACC</u>-TCCAGCAAACTCTTATATTC-3' |
| P4 | 5'-TAG<u>ACGCGT</u>-ACCCAATCAACCCAGTACAAG-3' |
| CamF | 5'-GCT<u>GGTTACC</u>-TAAGAGGTTCCAACTTTCAC-3' |
| CamR | 5'-CTA<u>GGTTACC</u>-TTTAAGGGCACCAATAACTG-3' |

Figure 1:
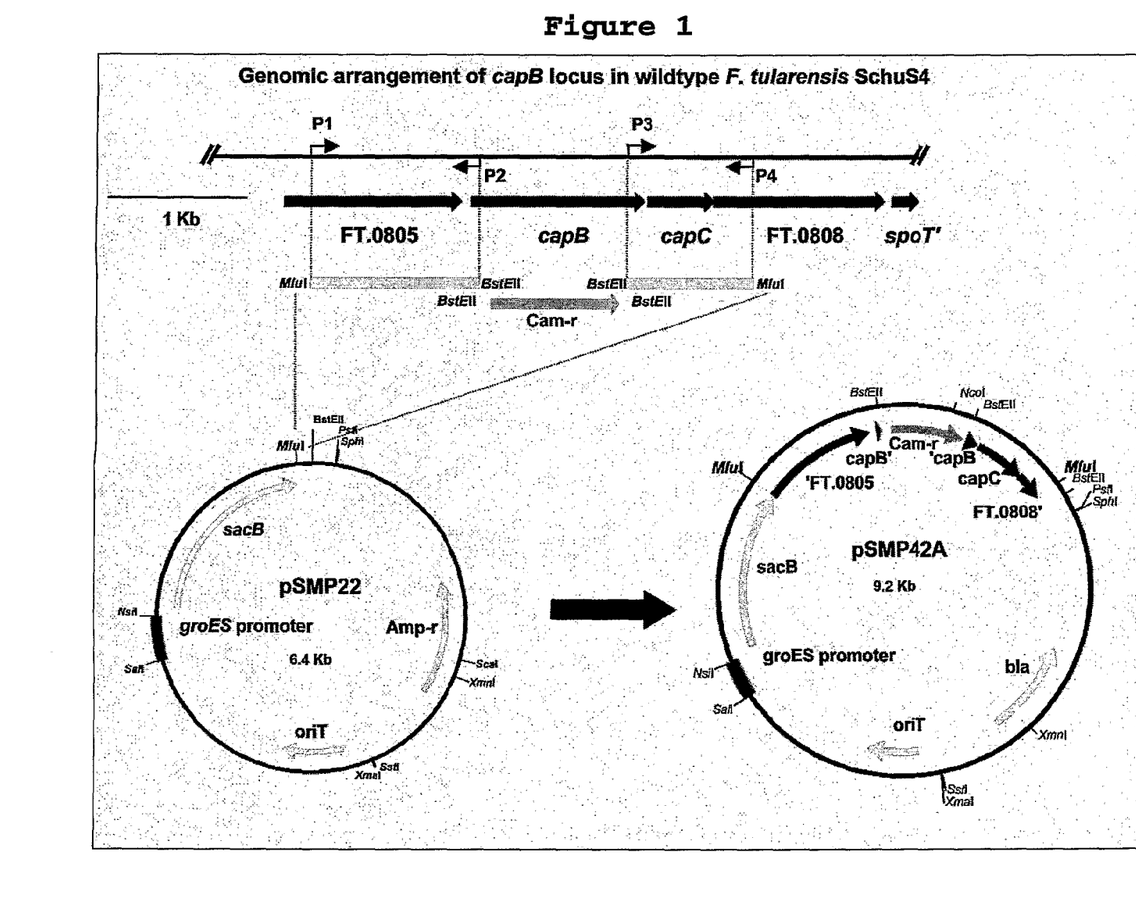
FIG. 1 shows the strategy for the construction of a suicide plasmid for the deletion of the capB gene from the *F. tularensis* subspecies *tularensis* strain SchuS4.

The left and right flanks and the chloramphenicol resistance cassette were assembled as shown in FIG. 1, and cloned into the suicide plasmid pSMP22 to give the construct pSMP42. This gave a plasmid-borne mutant allele that could be used for recombinational exchange with the wild type chromosomal allele.

EXAMPLE 2

Generation of a F. tularensis Strain Deleted for capB

Figure 2:
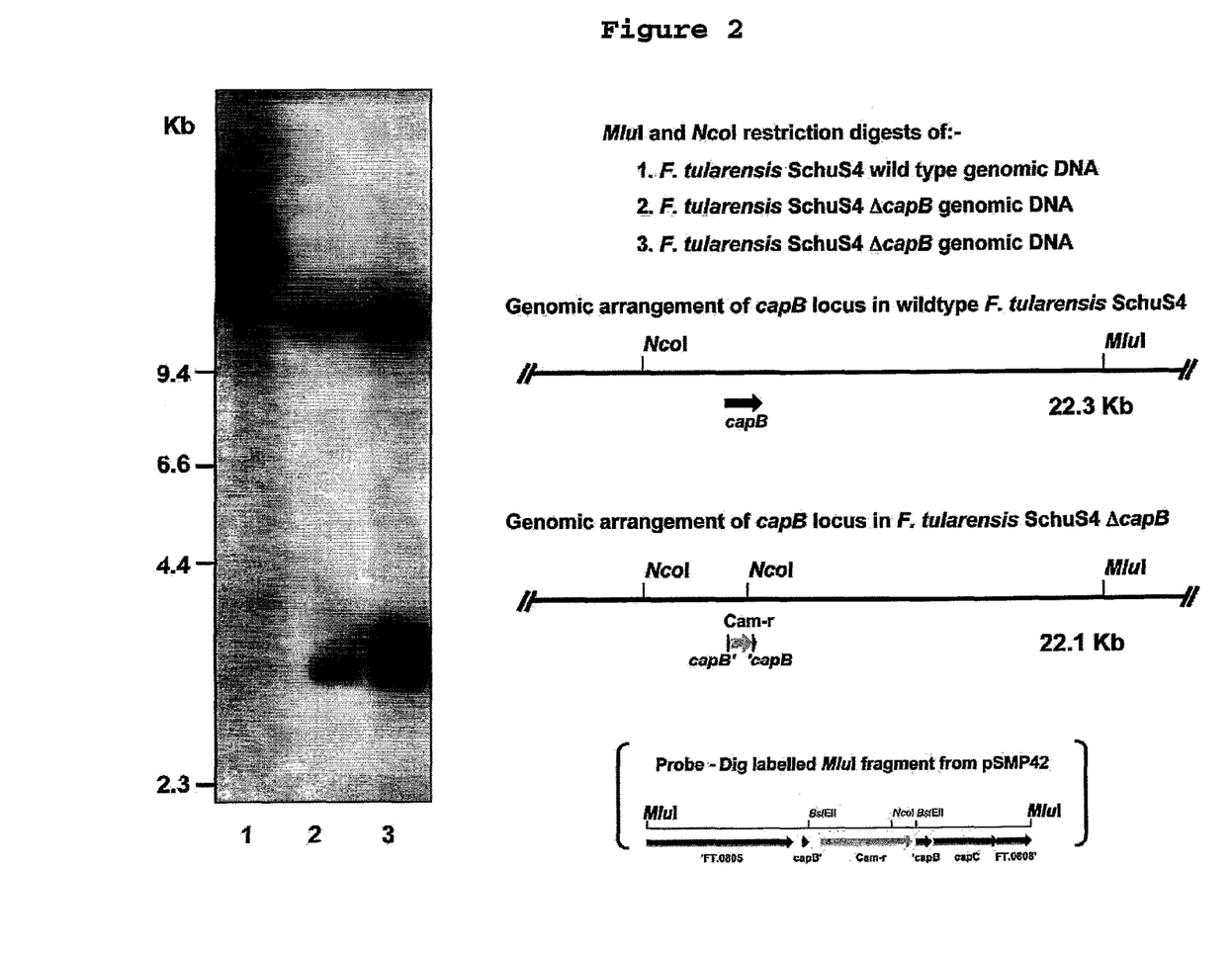
FIG. 2 shows a southern blot of genomic DNA from wild type and capB mutant strains of *F. tularensis* subspecies *tularensis* strain SchuS4.

The suicide plasmid pSMP42 was electroporated into the E. coli mobilising strain S-17 λpir. The plasmid was then introduced from the mobilising strain to F. tularensis subspecies tularensis strain SchuS4 by conjugal transfer. Transconjugants were selected on chloramphenicol and merodiploids arising from chromosomal integration of the suicide plasmid were resolved by plating on Thayer Martin agar containing sucrose at 5%. Allelic replacement mutants were confirmed by Southern blot analysis as shown in FIG. 2. Genomic DNA of wild type and capB deletion mutants (ΔcapB) of F. tularensis subspecies tularensis strain SchuS4 was digested with MluI and NcoI, separated by agarose gel electrophoresis and transferred to a nylon membrane. The MluI insert of pSMP42 was labelled with DIG-11-dUTP during PCR amplification with the primer pair P1/P4 and used as a probe to hybridise to the membrane. DNA fragments to which the probe hybridised were detected in a chemiluminescent assay (CSPD substrate, 30 min exposure, X-ray film). The ΔcapB mutant contained two hybridising fragments of 12.5 Kb and 3.2 Kb as shown in FIG. 2.

EXAMPLE 3

Comparison of Phenotype—Effect of Osmotic Stress

Figure 3:
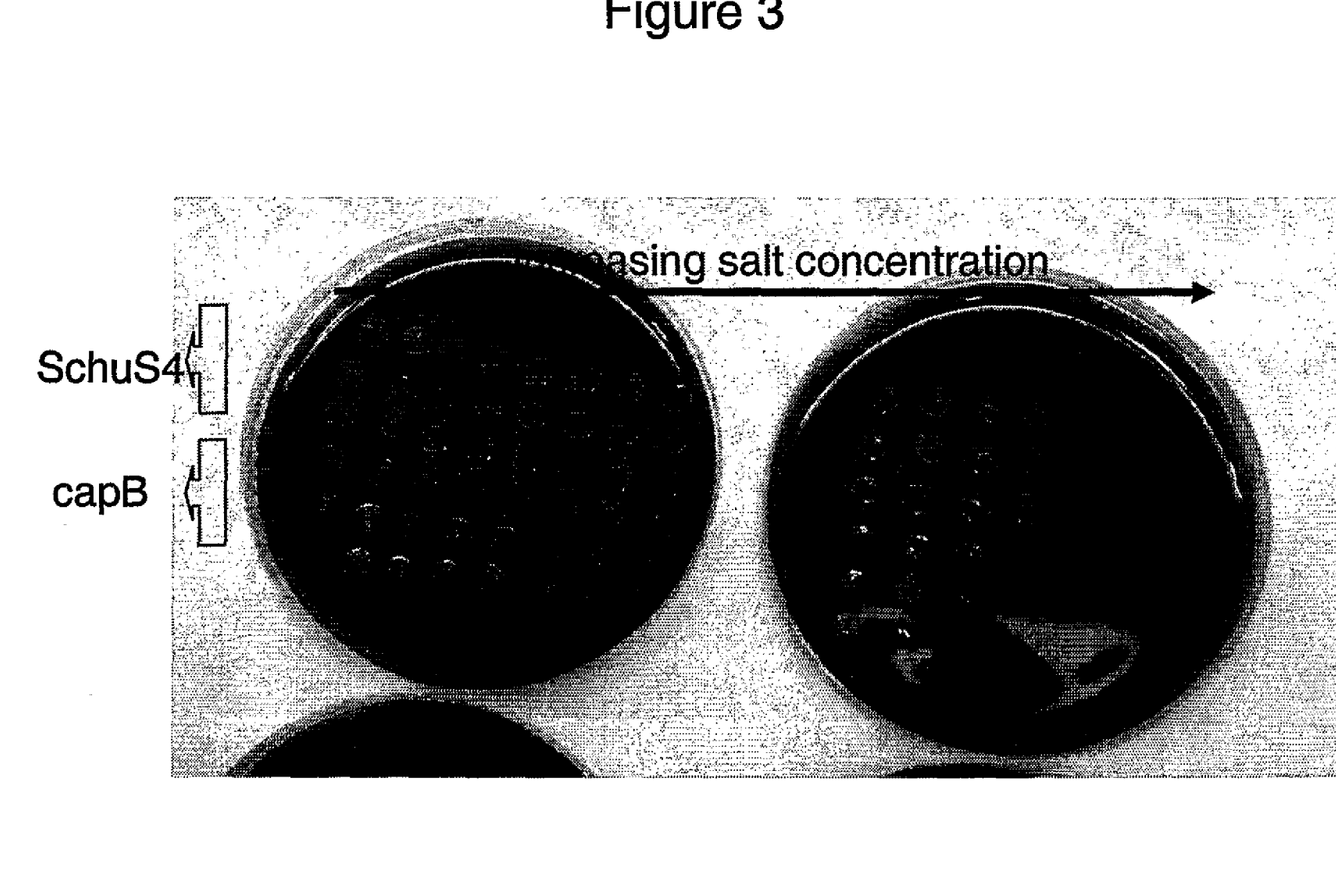
FIG. 3 shows the effects of osmotic stress on wild type *F. tularensis* subsp. *tularensis* strain SchuS4 and the ΔcapB mutant strain of the invention, when grown in a range of salt conditions.

F. tularensis subsp. tularensis strain SchuS4 ΔcapB and F. tularensis subsp. tularensis strain SchuS4 (wild type) were suspended in a range of salt (nacl) concentrations (up to 5M) and then plated onto BCGA media using 20 μl droplets. Bacterial growth was assessed after 72 hours and the results are portrayed in FIG. 3. It was apparent that, as compared with the wild type, SchuS4 ΔcapB grew less efficiently at the highest salt (5 M) concentration. It appeared that ΔcapB was also more sensitive at the low salt concentrations. This indicates that the ΔcapB mutant has a different phenotype to wild type F. tularensis and exhibits different growth characteristics in osmotic environments.

EXAMPLE 4

Determination of Virulence of a capB Mutant in the Mouse Model of Tularemia

Figure 4:
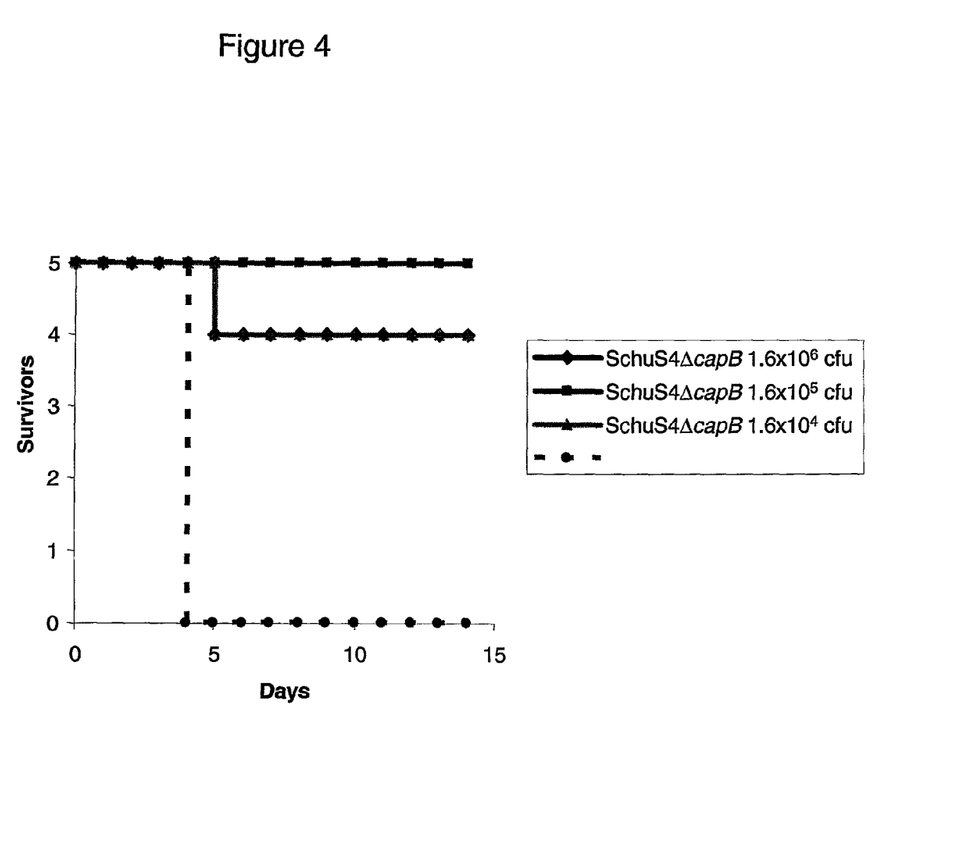
FIG. 4 shows survival data of BALB/c mice infected subcutaneously with wild type and caps mutant strains of *F. tularensis* subspecies *tularensis* strain SchuS4.

Several investigators have determined that the MLD of F. tularensis subspecies tularensis is ~10 colony forming units (CFU) in the BALB\c mouse, irrespective of route of administration. In order to determine whether capB is required for virulence, groups of six female BALB\c mice, aged 6-8 weeks, were infected subcutaneously with wild-type SchuS4 and ΔcapB SchuS4 strains of F. tularensis subspecies tularensis. As previously reported mice infected with $10^2$ (115) CFU of SchuS4 succumbed to infection by day 5 post-infection. In contrast, 100% of the mice infected with $1.6 \times 10^5$ and 80% (4 out of 5) of mice infected with $1.6 \times 10^6$ and $1.6 \times 10^4$ CFU of the ΔcapB isogenic strain survived as shown in FIG. 4. This level of survival following deletion of a single gene demonstrates that capB is an important gene in the virulence of F. tularensis subspecies tularensis.

EXAMPLE 5

Protection Afforded by a capB Mutant of Francisella tularensis

Figure 5:
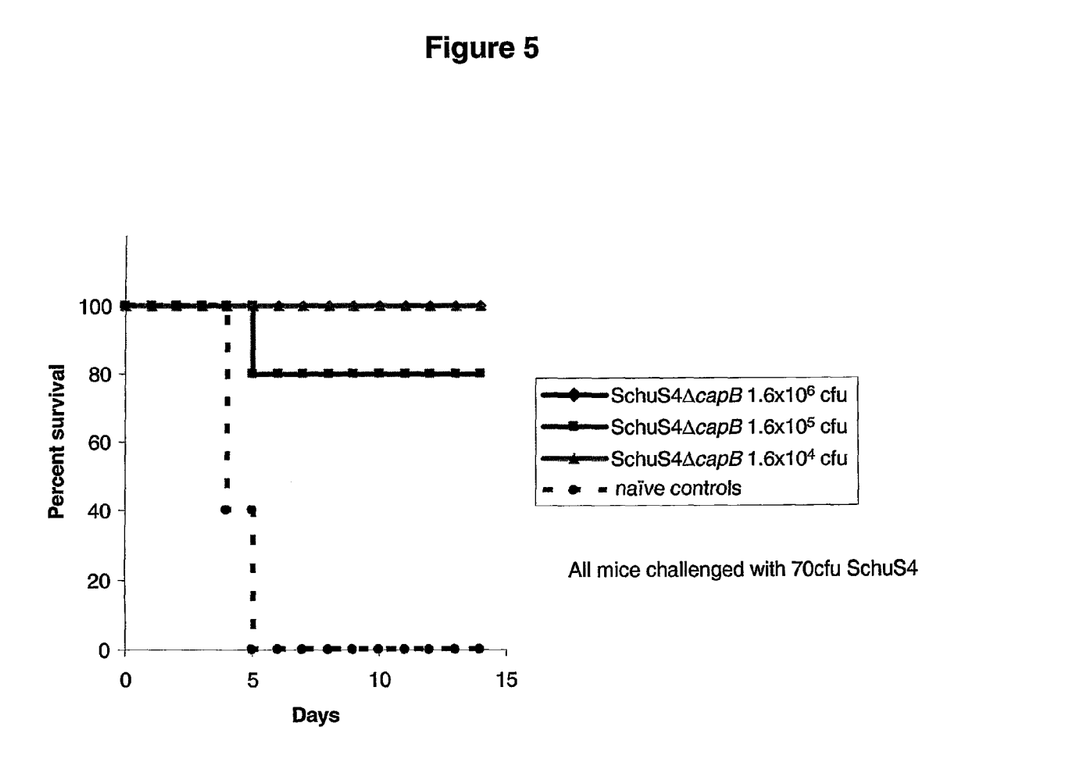
FIG. 5 shows survival data of BALB/c mice, administered with a capB mutant strain of *F. tularensis* subspecies *tularensis* strain SchuS4, and subsequently challenged with 70 mean lethal doses (MLD) of the virulent strain, *F. tularensis* subspecies *tularensis* strain SchuS4.

The chromosomal copy of the gene capB was deleted by allelic exchange as described in example 1 and 2. Genetic analysis was performed to ensure that the gene was removed (as per example 2) and a clonal population of the resultant strain was prepared. Upon subcutaneous administration to female Balb/c mice (6-8 weeks), $1.6 \times 10^5$ bacteria of the ΔcapB mutant strain failed to cause death in all five mice. This is in contrast to the parental wild-type strain of which only 115 bacteria were required to kill all 5 mice of a control group in 5 days. 46 days after immunisation with the capB negative strain, survivors of the infection detailed in Example 4 were challenged with 70 mean lethal doses (MLD) of a virulent strain of F. tularensis (SchuS4 strain). Non-immunised (naïve controls) mice succumbed to infection and died within 5 days whereas mice immunised with the capB mutant were protected and did not die as shown in FIG. 5.

EXAMPLE 6

Survival Against Virulent Challenge

Figure 6:
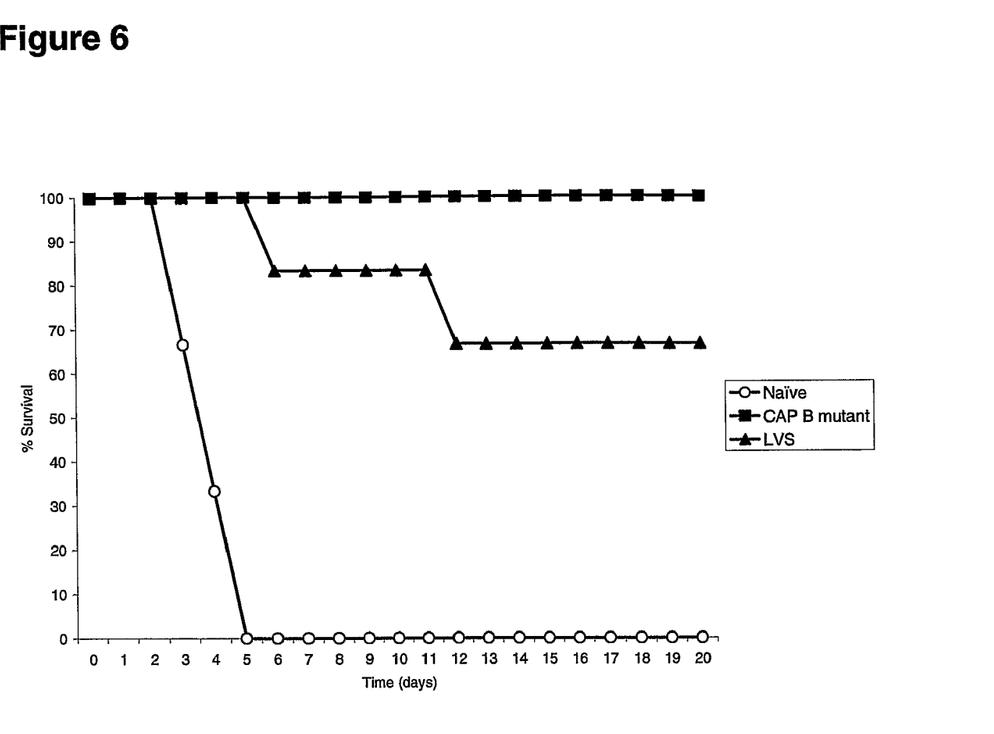
FIG. 6 shows survival data of Female BALB/c mice (6-8 weeks old), injected subcutaneously with 100 μl of PBS containing $10^4$ CFU *F. tularensis* subsp. *tularensis* strain SchuS4 ΔcapB, *F. tularensis* live vaccine strain (LVS) or PBS alone and eight weeks later challenged with $10^4$ CFU administered by the subcutaneous route.

Female BALB/c mice (6-8 weeks old) were injected subcutaneously with 100 μl of PBS containing $10^3$ CFU F. tularensis subsp. tularensis strain SchuS4 ΔcapB (prepared as described above), F. tularensis live vaccine strain (LVS) or PBS alone. Eight weeks later mice were challenged with $10^4$ CFU wild type F. tularensis subsp. tularensis strain SchuS4 administered by the subcutaneous route. Survival data, shown in FIG. 6, clearly indicates that superior protection is afforded by the capB deletion mutant than the live vaccine strain, and that 100% survival was observed.

EXAMPLE 7

Colonisation and Clearance In Vivo of F. tularensis Strains

Figure 7:
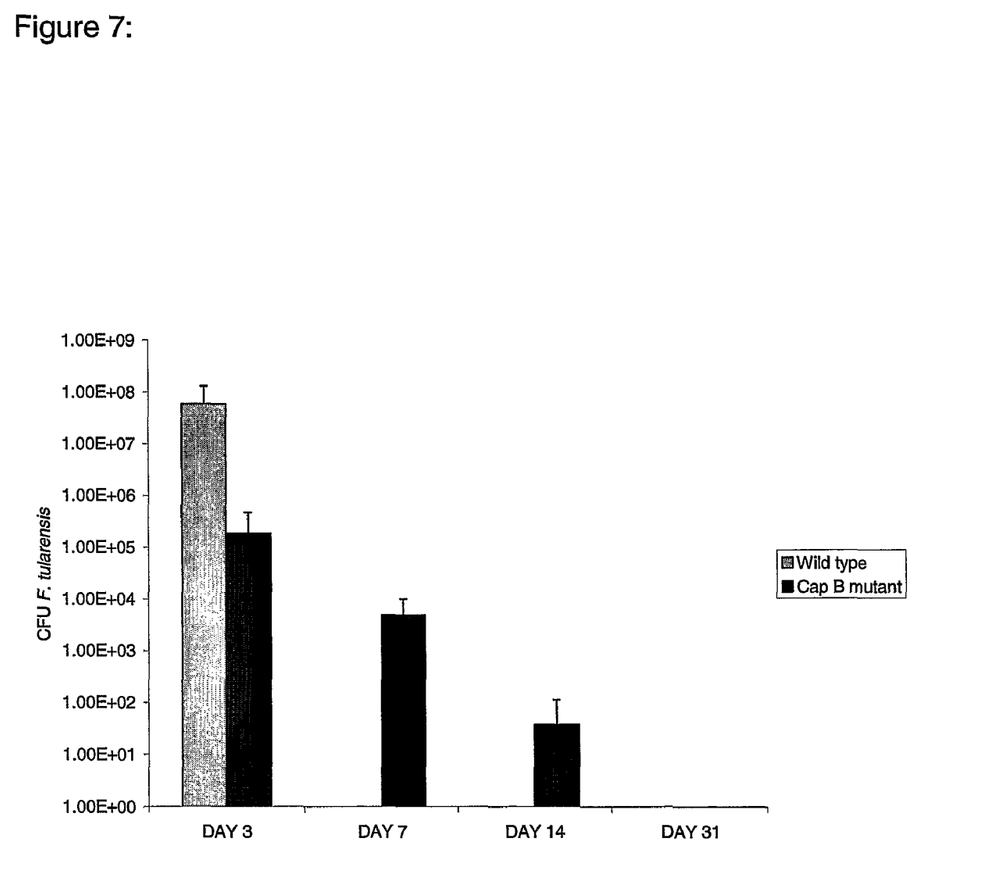
FIG. 7 shows a graph depicting the colonization and clearance of bacteria from the spleens of mice administered with either wild type *F. tularensis* subsp. *tularensis* strain SchuS4 or the ΔcapB mutant strain of the present invention.

Female BALB/c mice (6-8 weeks old) were injected subcutaneously with 100 μl of PBS containing $10^4$ CFU wild type F. tularensis subsp. tularensis strain SchuS4 or F. tularensis subsp. tularensis strain SchuS4 ΔcapB. Groups of 4 mice were killed 3, 7, 14 and 31 days following inoculation of the bacteria. Spleens were removed and the number of bacteria per spleen determined by serial dilution in PBS followed by microbiological culture on BCGA agar plates for 96 hours at 37 OC. None of the mice injected with wild type SchuS4 survived longer than five days post inoculation, which precluded determination of splenic bacterial burdens in these mice on days 7, 14 and 31 post inoculation. However, at day 3 post inoculation there was a highly significant (P<0.001) difference in the numbers of bacteria in the spleens of mice injected with wild type and the ΔcapB mutant; mice injected with F. tularensis subsp. tularensis strain SchuS4 ΔcapB had substantially lower numbers of bacteria in their spleens. Animals injected with F. tularensis subsp. tularensis strain SchuS4 ΔcapB steadily cleared the organism and no viable bacteria were detected in the spleens of these animals at 31 days post inoculation; indicating that they had effectively cleared the mutant. These results shown in FIG. 7 indicate that the capB mutant strain is less likely to cause latent infection after administration.

EXAMPLE 8

Figure 8:
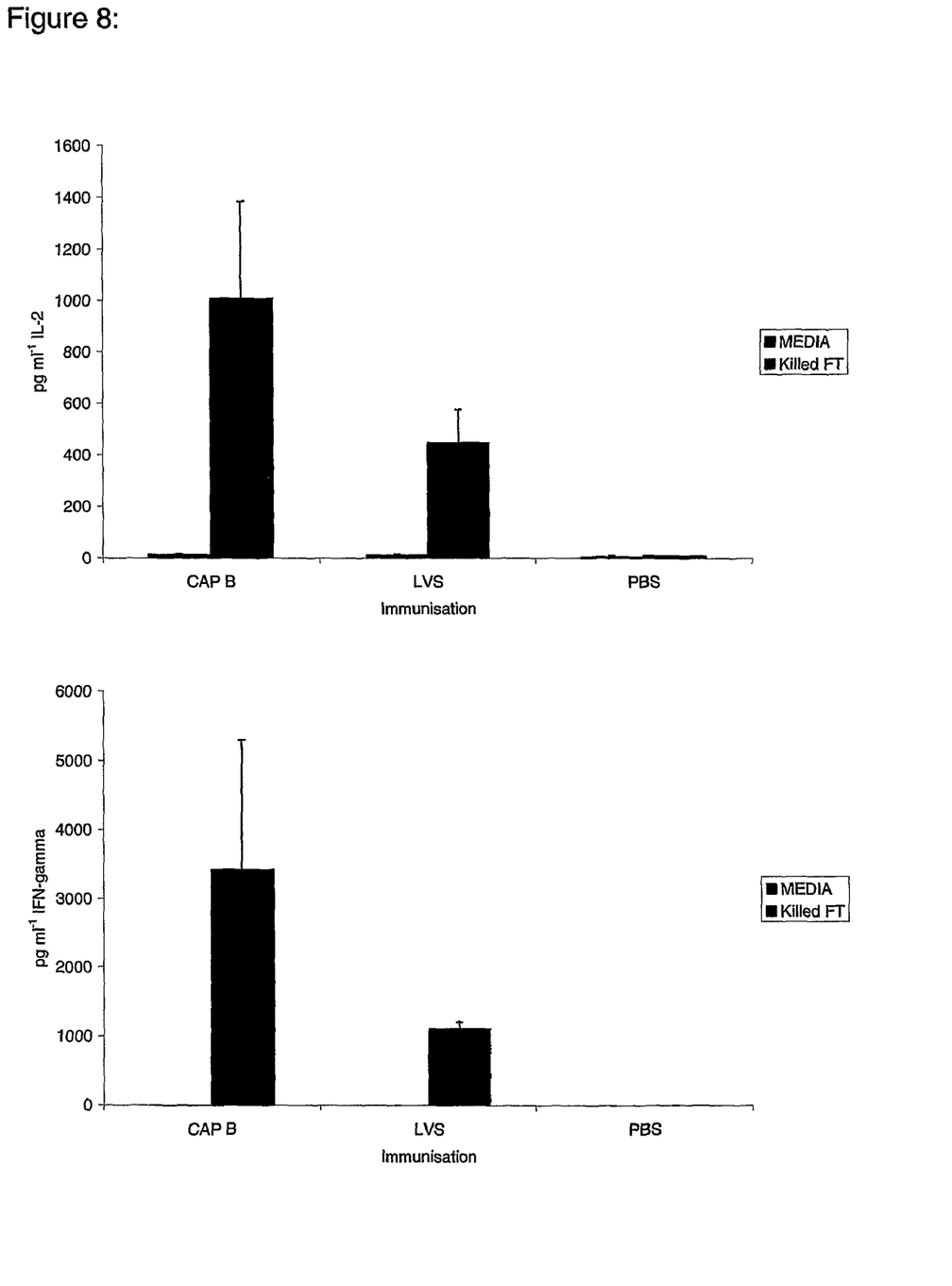
FIG. 8 shows a graph which quantifies the IL-2 and IFN-γ recall response of spleen cells harvested from mice immunized subcutaneously with 100 μl of PBS containing $10^4$ CFU *F. tularensis* subsp. *tularensis* strain SchuS4 ΔcapB, *F. tularensis* live vaccine strain (LVS) or PBS alone and then subsequently stimulated with wild type *F. tularensis* subsp. *tularensis* strain SchuS4.

IL-2 and IFN-γ Recall Response of Mice Immunized with the capB Mutant Strain of Example Female BALB/c mice (6-8 weeks old) were injected subcutaneously with 100 μl of PBS containing $10^4$ CFU F. tularensis subsp. *tularensis* strain SchuS4 ΔcapB, *F. tularensis* live vaccine strain (LVS) or PBS alone. 40 days later groups of immunised 4 mice were killed and their spleens removed. Single cell suspensions of spleen cells were prepared in culture media (RPMI-1640) (Sigma, UK) supplemented with 10% heat inactivated foetal bovine serum (FBS) (Sigma, UK); 1% penicillin/streptomycin/glutamine (Sigma, UK) and 50 μM 2-mercaptoethanol (Sigma, UK). Cells were stimulated overnight in triplicate with either heat killed *F. tularensis* subsp. *tularensis* strain SchuS4 (5 μg ml$^{-1}$ protein) in supplemented RPMI 1640 or supplemented RPMI 1640 alone. Il-2 and IFN-γ secretion from the cells was determined using cytokine bead array technology (BO Biosciences, Oxford UK). As compared with mice injected with PBS, spleen cells from animals immunized with SchuS4 ΔcapB or LVS secreted significant quantities of IL-2 and IFN-γ when re-stimulated in vitro with inactivated *F. tularensis* strain SchuS4. However, when spleen cells from animals immunized with SchuS4 ΔcapB or LVS were cocultured with media alone, no significant IL-2 or IFN-γ secretion was detected. These results are shown in FIG. 8.

The invention claimed is:

1. A method of stimulating an immune response against or treating infection caused by *Francisella tularensis*, comprising administering to an animal an effective amount of a strain of *Francisella tularensis* wherein capB or capC gene has been inactivated by deletion, and wherein administration of the effective amount of the strain is able to produce an immune response in an animal.

2. A method of stimulating an immune response against or treating infection caused by *Francisella tularensis*, comprising administering to an animal an effective amount of a pharmaceutical composition comprising a live strain of a *Francisella tularensis* wherein capB or capC gene has been inactivated by deletion, and wherein administration of the effective amount of the strain is able to produce an immune response in an animal, in combination with a pharmaceutically acceptable carrier.

3. The method of claim 1 wherein the strain of *Francisella tularensis* is a subspecies selected from the group consisting of *tularensis, holarctica* and *tularensis* SchuS4.

4. The method of claim 1 wherein the strain comprises a further deletion of a gene that encodes another component of the cell.

5. The method of claim 4 wherein the gene which encodes for another component of the cell is selected from the group consisting of FTT0918, FTT0919 and FTT1564.

6. The method of claim 4 wherein the gene that encodes for another component of the cell is a gene that encodes for a pilin subunit or is a gene that encodes for an enzyme in the purine pathway.

7. The method of claim 4 wherein the gene that encodes for another component of the cell is a gene selected from the group consisting of pilA, pilE, pilC, purA and purF.

8. The method of claim 2 wherein the strain of *Francisella tularensis* is a subspecies selected from the group consisting of *tularensis, holarctica* and *tularensis* SchuS4.

\* \* \* \* \*

UNITED STATES PATENT AND TRADEMARK OFFICE
CERTIFICATE OF CORRECTION

PATENT NO. : 8,323,664 B2
APPLICATION NO. : 12/374888
DATED : December 4, 2012
INVENTOR(S) : Stephen Lloyd Michell, Petra Claire Farquhar Oyston and Richard William Titball It is certified that error appears in the above-identified patent and that said Letters Patent is hereby corrected as shown below:

Title page, item (75), Inventors, "Stephen Lloyd Mitchell" should read --Stephen Lloyd Michell--

Signed and Sealed this
Twelfth Day of March, 2013

Teresa Stanek Rea
*Acting Director of the United States Patent and Trademark Office*